United States Patent [19]
Drent et al.

[11] Patent Number: 5,952,522
[45] Date of Patent: *Sep. 14, 1999

[54] PROCESS FOR THE CARBONYLATION OF ACETYLENICALLY UNSATURATED COMPOUNDS

[75] Inventors: Eit Drent; Willem Wabe Jager, both of Amsterdam, Netherlands

[73] Assignee: Shell Oil Company, Houston, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/768,419

[22] Filed: Dec. 18, 1996

[30] Foreign Application Priority Data

Dec. 29, 1995 [EP] European Pat. Off. .............. 95203670

[51] Int. Cl.$^6$ ...................................................... C07C 67/36
[52] U.S. Cl. .......................... 560/207; 562/497; 562/522; 560/232
[58] Field of Search .................................... 560/207, 232; 562/497, 522

[56] References Cited

U.S. PATENT DOCUMENTS 4,739,109  4/1988  Drent ...................................... 560/207

FOREIGN PATENT DOCUMENTS

WO 94/21585  9/1994  WIPO .
WO 95/03269  2/1995  WIPO .

*Primary Examiner*—Paul J. Killos

[57] ABSTRACT

A process is disclosed for the carbonylation of acetylenically unsaturated compounds by reaction with carbon monoxide and a co-reactant in the presence of a catalyst system based on: (a) a source of platinum; (b) a bidentate ligand of the formula $R^1R^2M^1$-R-$M^2R^3R^4$, wherein $M^1$ and $M^2$ independently are P, As or Sb, R represents a bivalent substituted or non-substituted bridging group containing from 1 to 5 atoms in the bridge, $R^1$ and $R^2$ together are a substituted or non-substituted bivalent group whereby the two free valencies are linked to $M^1$, and $R^3$ and $R^4$ together are a substituted or non-substituted bivalent group whereby the two free valencies are linked to $M^2$ or $R^3$ and $R^4$ independently are substituted or non-substituted hydrocarbyl groups; and (c) a source of anions.

15 Claims, No Drawings

PROCESS FOR THE CARBONYLATION OF ACETYLENICALLY UNSATURATED COMPOUNDS

FIELD OF THE INVENTION

The invention relates to a process for the carbonylation of acetylenically unsaturated compounds by reaction with carbon monoxide and a co-reactant in the presence of a platinum-containing catalyst.

BACKGROUND TO THE INVENTION

An interesting feature of carbonylation reactions whereby as starting material an acetylenically unsaturated compound is used, consists in that carbonylated products are formed which still contain a reactive unsaturated bond in their molecules. Accordingly, these products are suitable as monomers for the manufacture of functionalized polymers and as intermediates in the preparation of various valuable chemicals.

In the investigation of carbonylation reactions in which as starting materials acetylenically unsaturated compounds are used, the emphasis so far has mainly been on the preparation of (branched) carbonylation products using palladium-based catalyst systems. For instance, in EP-A-0, 186,228 and WO 95/03269 a process of this type is described.

In view of the fact that for a number of outlets the availability of linear, rather than branched carbonylated products would be desirable, e.g. in the preparation of components of detergent compositions, efforts have been made to increase the selectivity with respect to linear carbonylation products. Thus, in WO 94/21585 a process is described, wherein use is made of a catalyst system based on platinum, a bisphosphine ligand and a source of anions, typically a strong acid. Unfortunately, the activity of this catalyst system is somewhat low, being in the order of 20 to 200 mole product per mole Pt per hour for acetylene as reactant.

SUMMARY OF THE INVENTION

It has now been found that by using a platinum-containing catalyst system which is further based on a specific category of bidentate ligands, the formation of linear carbonylation products at a high production rate is greatly enhanced. Moreover, it has been found that this type of catalyst system is eminently suitable for the preparation of linear, unsaturated aldehydes by hydroformylation of acetylenically unsaturated feed stocks. Finally, this type of catalyst has also been found suitable for the preparation of carbonylation-hydroformylation products, e.g., esters of formylcarboxylic acids.

The invention may be defined as relating to a process for the carbonylation of acetylenically unsaturated compounds by reaction with carbon monoxide and a co-reactant in the presence of a catalyst system based on: (a) a source of platinum; (b) a bidentate ligand of the formula $R^1R^2M^1$-R-$M^2R^3R^4$, wherein $M^1$ and $M^2$ independently are P, As or Sb, R represents a bivalent substituted or non-substituted bridging group containing from 1 to 5 atoms in the bridge, $R^1$ and $R^2$ together are a substituted or non-substituted bivalent group whereby the two free valencies are linked to $M^1$, and $R^3$ and $R^4$ together are a substituted or non-substituted bivalent group whereby the two free valencies are linked to $M^2$ or $R^3$ and $R^4$ independently are substituted or non-substituted hydrocarbyl groups; and (c) a source of anions.

It is believed that the process of the invention involves the formation of an intermediate complex whereby the platinum metal ion coordinates with the atoms $M^1$ and $M^2$ of the bidentate ligand, i.e., component (b), and with the acetylenically unsaturated compound.

As regards the source of platinum, i.e., component (a) of the catalyst system, any platinum compound allowing complexing between the metal and the bidentate ligand may be used. Suitable compounds are for instance, metallic platinum, zero valent platinum complexes, such as tetrkkis (triphenylphosphine)platinum; and tetra- or divalent platinum salts. In particular platinum(II) salts are suitable, such as dipotassium tetracyanoplatinate, disodium tetracyanoplatinate, dipotassium tetrachloroplatinate, potassium trichloro (ethylene) platinate, sodium trichloro (ethylene) platinate, platinum-bis(cyanobenzene) disulphate and platinum-bis(triphenylphosphine) disulphate. Salts of platinum with carboxylic acids, in particular with carboxylic acids having from 2 to 12 carbon atoms, are also suitable, for example platinum diacetate, platinum dipropionate and platinum dihexanoate.

Organic platinum(H) complexes are preferably applied as source of platinum, platinum(II) acetylacetonate being particularly suitable.

Regarding the bidentate ligand constituting component (b) of the catalyst system, $M^1$ and $M^2$ preferably both represent phosphorus atoms. The bivalent bridging group R typically is an organic group, inclusive organometallic groups such as ferrocylene, connecting the atoms $M^1$ and $M^2$ through carbon atoms. Usually all bridging atoms are carbon atoms, optionally with hetero-atoms (other than H or C) thereto attached. Preferably, R represents an alkylene group containing from 1 to 3 carbon atoms in the bridge, in particular an ethylene group.

The bivalent substituted or non-substituted group, represented by $R^1$ together with $R^2$, preferably contains from 5 to 9 atoms. Examples of suitable bivalent groups are 1,6-hexylene, 1,6-heptylene, 1,5-octylene, etc. Together with $M^1$, this group forms a phosphacycloalkyl group. Preferably, $R^1$ together with $R^2$ represent a bivalent substituted or non-substituted cyclic group. Together with $M^1$, this preferred group forms a phosphabi-cycloalkyl group. Examples of suitable bivalent cyclic groups are 1,4-cyclohexylene, 1,4-cycloheptylene, 1,2-cyclooctylene, 1,4-cyclooctylene, 1,5-cyclooctylene and 2-methyl-1,5-cyclooctylenegroups.

$R^3$ and $R^4$ may independently represent any substituted or non-substituted hydrocarbyl group, such as alkyl, aryl, alkaryl or aralkyl groups. Preferably, $R^3$ and $R^4$ together have the same meaning as $R^1$ together with $R^2$.

Suitable substituents in case any of R, or $R^1$ to $R^4$ is substituted are preferably selected from the group consisting of halogen atoms, and cyano, alkoxy, amino and alkylamino groups. The alkyl groups in the alkoxy and alkylamino groups preferably each contain from 1 to 4 carbon atoms.

Particularly preferred bidentate ligands are the [3,3,1] and [4,2,1] isomers of 1,2-P,P'-bis(9-phosphabicyclononyl) ethane and the [3,3,1] and [4,2,1] isomers of 1,2-P,P'-bis (dimethyl-9-phosphabicyclononyl)ethane.

For the preparation of the catalyst systems of the invention, the amount of bidentate ligand of formula is generally applied in some excess of the amount of platinum, expressed as moles of bidentate ligand per mole atom of platinum. The active species, however, is believed to be based on an equimolar amount of bidentate ligand per mole platinum. Thus, the molar amount of bidentate ligand per mole of platinum is suitably in the range of 1 to 3, preferably in the range of 1 to 2. In the presence of oxygen, slightly higher amounts may be beneficial.

The catalyst systems used in the process of the invention are further based on a source of anions, i.e., component (c). It is believed that the size of the anion and the distribution of electric charge in the anion significantly contribute to the stability of the catalyst system. Preferably, anions are used that are the conjugated base of acids having a pKa (measured at 18° C. in water) of less than 4. Catalysts based on these anions have a substantially improved activity.

Suitable anions include anions derived from Bronsted acids, in particular from carboxylic acids, such as 2,6-dichlorobenzoic acid, and 2,6-bis(trifluoromethyl)benzoic acid or trifluoroacetic acid; and from sulphonic acids, such as methanesulphonic acid, trifluoromethanesulphonic acid, etc.

Preferably, the anion is a "complex" anion, generated by a combination of a Bronsted acid and a Lewis acid. In case of a complex anion, recommended Bronsted acids include hydrohalogenic acids, such as HF and HCl and, in particular, sulphonic acids, such as methanesulphonic acid, trifluoromethanesulphonic acid, trichloromethanesulphonic acid and the like. Recommended Lewis acids are, for example, $SnCl_2$, $SnF_2$, $GeCl_2$, $Sn(CF_3SO_3)_2$ and $BF_3$. Examples of preferred complex anion-generating combinations are therefore $H[SnCl_2.CH_3SO_3]$ and $H[SnCl_2.CF_3SO_3]$.

The molar amount of anion per mole of platinum is conveniently selected in the range of 1 to 12. Preferably the anion is applied in a molar amount per mole of platinum in the range of 1 to 8.

The process of the invention is carried out with catalytic amounts of the catalyst system, i.e. per mole of acetylenically unsaturated compound, $10^{-8}$ to $10^{-1}$ mole of platinum is present, preferably from $10^{-7}$ to $10^{-2}$, on the same basis.

The acetylenically unsaturated compounds which may suitably be employed as starting material in the process of the invention, include compounds containing from 2 to 20 carbon atoms, optionally containing one or more inert substituents, such as halogen atoms or hydroxygroups.

Preferably, the acetylenically unsaturated compounds has from 2 to 8 carbon atoms per molecule. The acetylenically unsaturated bond is usually the only carbon-carbon unsaturation in the molecule. In view of the envisaged preparation of mainly linear carbonylated products, it is preferably located at a terminal position.

Examples of suitable acetylenically unsaturated compounds are acetylene(=ethyne), methylacetylene (=propyne), 1-butyne, 1-pentyne, 1-hexyne, 1-octyne, phenylacetylene and 3-hydroxybutyne.

Suitable co-reactants in the process of the invention are hydrogen-containing compounds whereby a carbon monoxide molecule and at least one acetylenically unsaturated compound can be inserted into the bond between the hydrogen atom and the molecule of the co-reactant. Examples thereof include nucleophilic compounds containing at least one mobile hydrogen atom.

Preferred nucleophilic compounds include: water and alcohols, e.g., monohydric alcohols, such as methanol, ethanol, isopropanol and 1-butanol, and polyhydric alcohols, such as ethyleneglycol, 1,4-butanediol and glycerol; thiols; primary or secondary amines or amides; phenols and carboxylic acids, for example acetic acid, pivalic acid and propionic acid. Monohydric alcohols having from 1 to 6 carbon atoms are preferred, in particular methanol and butanol.

Another category of suitable co-reactants comprises hydride sources such as molecular hydrogen and compounds capable of generating molecular hydrogen. In particular for embodiments of the process whereby an acetylenically unsaturated compound is hydroformylated, molecular hydrogen is a preferred co-reactant.

Finally, also a combination of a nucleophilic compound and a hydride source as defined above may be used, to prepare a carbonylation-hydroformylation product.

The carbonylation process of the invention is generally carried out at a reaction temperature in the range of 40 to 200° C., more often at a temperature in the range of 50 to 160° C.

The total reaction pressure is usually in the range of 5 to 150 bar absolute (bara). Pressures between 10 and 80 bara and in particular between 30 and 60 bara are preferred.

In carbonylation reactions of the hydroformylation type, the total pressure is usually the sum of the partial pressures of carbon monoxide and hydrogen. The molar ratio between these gases may vary, but is conveniently maintained in the range of 1:2 to 2:1. Preferably, substantially equimolar amounts of carbon monoxide and hydrogen are used.

In other carbonylation reactions, involving no hydrogen, or only insignificant amounts thereof, the total pressure is roughly the same as the carbon monoxide pressure.

The process of the invention may be carried out in the absence of a separate diluent or solvent, if so desired. However, it is often convenient to have a liquid diluent or solvent present at the beginning of the reaction, e.g. if a volatile acetylenic starting material is used, or if the reaction requires a relatively long induction period and continued thorough mixing of the reactants is desirable.

Suitable solvents are, in particular, aprotic compounds such as ethers or ketones, for example 2,5,8-trioxanonane, diethylether, acetone and methyl ethylketone.

The invention is further illustrated by the following examples. The abbreviations used in the examples, have the following meanings:

| MeOH | = | methanol | BuOH | = | butanol |
|------|---|----------|------|---|---------|
| PA | = | platinum(II) (acetylacetonate)$_2$ | | | |
| BPBNE | = | an isomeric mixture of 1,2-P,P'-bis(9-phosphabicyclononyl)ethane | | | |
| (T)MS | = | (trifluoro)methanesulphonic acid | | | |

EXAMPLE 1

(a) A 300 mL "Hastelloy C" (trademark) magnetically stirred autoclave was charged with acetylene (1.4 bara), 30 mL of t-BuOH, 0.25 mmol of PA, 0.3 mmol of BPBNE, 0.4 mmol of MS, 0.4 mmol of $SnCl_2$ and 30 mL of 2,5,8-trioxanonane.

The autoclave was pressurized with 15 bara carbon monoxide and then sealed. The temperature of the mixture was raised to 115° C. After a reaction period of 15 minutes, the reaction was discontinued and the contents of the autoclave were cooled. The acetylene conversion was 100%. The product consisted of t-butyl acrylate, prepared at a rate of 2240 mol/mol.h.

(b) The example was repeated, using 30 bara carbon monoxide. t-Butyl acrylate was now prepared at an average rate of 3050 mol/mol.h.

(c) The example was repeated, using 40 bara carbon monoxide. t-Butyl acrylate was now prepared at a rate of 5300 mol/mol.h.

These examples illustrate the excellent yield obtainable by the process of the invention, in particular at higher carbon monoxide pressures.

EXAMPLE 2

(a) An autoclave of the type as described in Example 1 was charged with acetylene (1.4 bara), 0.28 mol of water, 0.25 mmol of PA, 0.3 mmol of BPBNE, 0.4 mmol of MS, 0.4 mmol of SnCl$_2$ and 50 mL of 2,5,8-trioxanonane.

The autoclave was pressurized with carbon monoxide (30 bara) and then sealed. The temperature of the mixture was raised to 115° C.

After a reaction period of 1 hour, the reaction was discontinued and the contents of the autoclave were cooled. The acetylene conversion was 100%. The product consisted of acrylic acid, prepared at an average rate of 620 mol/mol.h. (b) The example was repeated, using 0.4 mmol HCl instead of MS. Acrylic acid was now prepared at an average rate of 1400 mol/mol.h.

Again a high rate was achieved, now using water as nucleophilic reagent.

EXAMPLE 3

An autoclave of the type as described in Example 1 was charged with 20 mL methyl acetylene, 20 mL MeOH, 0.25 mmol of PA, 0.3 mmol of BPBNE, 0.4 mmol of MS, 0.4 mmol of SnCl$_2$ and 40 mL of 2,5,8-trioxanonane.

The autoclave was pressurized with carbon monoxide (50 bara) and then sealed. The temperature of the mixture was raised to 115° C.

After a reaction period of 2.5 hours, the reaction was discontinued and the contents of the autoclave were cooled. The methyl acetylene conversion was 100%. The product consisted of methyl crotonate with a selectivity of 98%, prepared at an average rate of 400 mol/mol.h.

This example illustrates that the process of the invention combines excellent selectivity towards linear products with a good rate.

COMPARATIVE EXAMPLE A

Example 1(c) was repeated, however, using 0.3 mmol 1,2-bis(diphenylphosphino)ethane instead of BPBNE as ligand. After 5 hours, a conversion of only 40% was achieved. The rate at which butyl acrylate was produced, was less than 30 mol/mol.h. Moreover, butyl acrylate was produced at a selectivity of only 50%, the remainder being primarily composed of 1,1-dibutoxyethane.

COMPARATIVE EXAMPLE B

Example 1(c) was repeated, however, using 0.3 mmol 1,2-bis(dicyclohexylphosphino)ethane instead of BPBNE as ligand. After 5 hours, a conversion of only 20% was achieved. The rate at which butyl acrylate was produced, was about 16 mol/mol.h. Moreover, butyl acrylate was now produced at a selectivity of only 30%, the remainder being primarily composed of 1,1-dibutoxyethane.

EXAMPLE 4

An autoclave of the type as described in Example 1 was charged with acetylene (1.4 bara), 0.25 mmol of PA, 0.6 mmol of BPBNE, 0.5 mmol of TMS, 0.5 mmol of SnCl$_2$ and 40 mL of 2,5,8-trioxanonane.

The autoclave was pressurized with carbon monoxide (30 bara) and hydrogen (30 bara) and then sealed. The temperature of the mixture was raised to 88° C. After an induction period of 5 hours, followed by a reaction period of 10 hours, the reaction was discontinued and the contents of the autoclave were cooled.

The acetylene conversion was 100%. The product consisted of acrolein (22%) and propionaldehyde (78%), produced at a rate of 100 mol/mol. hr.

This example illustrates that the process of the invention is suitable for carbonylation reactions of the hydroformylation type, whereby an alkyne is converted into an ethylenically unsaturated aldehyde.

EXAMPLE 5

To the reaction mixture, obtained in Example 4, 10 mL of 1-pentyne was added. The autoclave was pressurized with carbon monoxide (30 bara) and hydrogen (30 bara) and subsequently sealed. The temperature of the mixture was increased to 84° C. After 10 hours reaction period, the reaction was discontinued and the contents of the autoclave were cooled to ambient temperature.

GLC analysis showed that 70% of 1-pentyne had been converted to hexenals. The selectivity with respect to 2-hexenal was 86%, to 3-hexenal 1% and to hexanal 13%. The linearity of the aldehydes was 100%, produced at a rate of 30 mol/mol.hr.

As in example 4, this example illustrates that the process of the invention is suitably applied for hydroformylation type carbonylation reactions, with an alkyne as feed, into unsaturated hydroformylation products. Moreover, selectivity towards linear products is maintained, even when the catalyst is used for a second time.

EXAMPLE 6

An autoclave of the type as described in Example 1 was charged with acetylene (1.4 bara), 50 mL t-BuOH, 0.25 mmol of PA, 0.3 mmol of BPBNE, 0.3 mmol of HCl, and 0.3 mmol of SnCl$_2$.

The autoclave was pressurized with carbon monoxide and molecular hydrogen (30 and 30 bara respectively) and then sealed. The temperature of the mixture was raised to 100° C.

After a reaction period of 2.5 hours, the reaction was discontinued and the contents of the autoclave were cooled. The acetylene conversion was 100%. The product consisted of 60 mole % t-butyl 1-formylpropionate, 30 mole % propanal and 10 mole % t-butyl propionate, prepared at an average rate of 250 mol/mol.h.

EXAMPLE 7

Example 6 was repeated, however, using carbon monoxide and molecular hydrogen at 40 and 20 bara respectively.

After a reaction period of 1 hour, the reaction was discontinued and the contents of the autoclave were cooled. The acetylene conversion was 100%. The product consisted of 74 mole % t-butyl 1-formylpropionate, 1 mole % propanal and 25 mole % t-butyl propionate, prepared at an average rate of 620 mol/mol.h.

EXAMPLE 8

Example 7 was repeated, however, using 50 ml of 1-BuOH.

After a reaction period of 6 hours, the reaction was discontinued and the contents of the autoclave were cooled. The acetylene conversion was 100%. The product consisted of 60 mole % butanol acetal of butyl 1-formylpropionate, about 5 mole % butanol acetal of propanal and 35 mole % t-butyl propionate, prepared at an average rate of 100 mol/mol.h.

These examples illustrate that the process of the invention may also be used to prepare carbonylation-hydroformylation products with a good rate.

We claim:

1. A process for the carbonylation of acetylenically unsaturated compounds by reaction with carbon monoxide and a co-reactant in the presence of a catalyst system based on:

(a) a source of platinum;
   (b) a bidentate ligand of the formula $R^1R^2M^1$-R-$M^2R^3R^4$, wherein $M^1$ and $M^2$ independently are P, As or Sb, R represents a bivalent substituted or non-substituted bridging group containing from 1 to 5 atoms in the bridge, $R^1$ and $R^2$ together are a substituted or non-substituted bivalent group whereby the two free valencies are linked to $M^1$, and $R^3$ and $R^4$ together are a substituted or non-substituted bivalent group whereby the two free valencies are linked to $M^2$ or $R^3$ and $R^4$ independently are substituted or non-substituted hydrocarbyl groups; and
   (c) a source of anions.

2. The process of claim 1 wherein the acetylenically unsaturated compound is an alkyne having from 2 to 20 carbon atoms.

3. The process of claim 1 wherein the acetylenically unsaturated compound is an alkyne having from 2 to 8 carbon atoms.

4. The process of claim 1 wherein the co-reactant is a hydride source and/or a nucleophilic compound having at least one mobile hydrogen atom.

5. The process of claim 4 wherein the nucleophilic compound is an alcohol having from 1 to 6 carbon atoms.

6. The process of claim 4 wherein the co-reactant is molecular hydrogen.

7. The process of claim 4 wherein the co-reactant is both a an alcohol having from 1 to 6 carbon atoms and molecular hydrogen.

8. The process of claim 1 wherein component (a) of that catalyst system is based on an organic platinum complex.

9. The process of claim 1 wherein component (b) of that catalyst system is based on a bidentate ligand of formula wherein $M^1$ and $M^2$ both represent phosphorus atoms.

10. The process of claim 1 wherein R in the bidentate ligand of formula represents an alkylene group containing from 1 to 3 carbon atoms in the bridge.

11. The process of claim 1 wherein in the bidentate ligand of formula, $R^1$ together with $R^2$, and $R^3$ together with $R^4$, represent a cycloalkylene group containing from 6 to 9 ring atoms.

12. The process of claim 1 wherein the bidentate ligand is the [3,3,1] and/or [4,2,1] isomer of 1,2-P,P'-bis(9-phosphabicyclononyl)ethane, or the [3,3,1] and/or [4,2,1] isomer of 1,2-P,P'-bis(dimethyl-9-phosphabicyclononyl)ethane.

13. The process as claim 1 wherein component (c) of the catalyst system is based on an anion having a pKa (measured at 18° C. in water) of less than 4.

14. The process of claim 13 wherein component (c) of the catalyst system is based on a combination of a Lewis acid and a Bronsted acid.

15. The process of claim 14 wherein the Lewis acid is tin(II) chloride.

* * * * *